(12) United States Patent
Steward, Jr.

(10) Patent No.: US 8,016,483 B2
(45) Date of Patent: Sep. 13, 2011

(54) POSITIONING APPARATUS FOR DENTAL X-RAY PROCEDURES

(75) Inventor: Curtis L. Steward, Jr., Sandwich, IL (US)

(73) Assignee: Dentsply International, Inc., York, PA (US)

( * ) Notice: Subject to any disclaimer, the term of this patent is extended or adjusted under 35 U.S.C. 154(b) by 106 days.

(21) Appl. No.: 12/583,866

(22) Filed: Aug. 27, 2009

(65) Prior Publication Data

US 2011/0051900 A1 Mar. 3, 2011

(51) Int. Cl.
*A61B 6/14* (2006.01)
(52) U.S. Cl. .......................... 378/170; 378/168
(58) Field of Classification Search ........... 378/168–170
See application file for complete search history.

(56) References Cited

U.S. PATENT DOCUMENTS

| 237,106 A | 9/1875 | Stevenson |
| 3,473,026 A | 10/1969 | Updegrave |
| 5,327,477 A | 7/1994 | Levy |
| 5,652,779 A | 7/1997 | Levy et al. |
| 2004/0170253 A1* | 9/2004 | Landis et al. ............. 378/168 |

* cited by examiner

*Primary Examiner* — Hoon Song
(74) *Attorney, Agent, or Firm* — Douglas J. Hura; Leana Levin; David A. Zdurne

(57) ABSTRACT

A dental bite block (20) and sensor holder (21) assembly (11) has a bite block (20) configured (31) to detachably affix to a sensor holder (21). Affixing surfaces (30, 31) are provided between the bite block (20) and the sensor holder (21) such that the sensor holder (21) is removably affixed to the bite block (20). An alternative guide arm (100) has more than one attachment site (101*a*, 101*b*) for removably affixing a sensor holder (102, 103, 104) to the guide arm (100).

14 Claims, 15 Drawing Sheets

US 8,016,483 B2

POSITIONING APPARATUS FOR DENTAL X-RAY PROCEDURES

TECHNICAL FIELD

The present invention is a sensor holder apparatus having a bite block and aiming ring mounted to a guide arm, for use during dental x-ray procedures. More particularly, the invention is a modular bite block and sensor holder assembly having a sensor support or guide arm, such that a given sensor can be used with bite blocks for different x-ray procedures. Also, provided is an improved aiming ring for use in dental x-ray procedures. Sensor holders of various designs can be removably affixed to more than one location on the support arm, facilitating a plurality of dental x-ray procedures.

BACKGROUND OF THE INVENTION

Dental radiographs are made using x-ray examination units, often including an x-ray cone or tube positioned proximate the patient and aligned to take x-rays of certain teeth. Dental x-ray sensors, including films, charge coupled devices, phosphor imaging plates or the like, often have a generally flat or plate-like configuration and standardized dimensions so that the sensor can be placed into the oral cavity.

The sensor is placed into the patient's mouth and held in place proximate to the tooth or teeth to be examined. The x-ray's are directed through the target teeth and then through the sensor. It has been found that proper orientation of the sensor is required to eliminate distortions and improper focus.

To ensure proper orientation of the sensor, sensor carriers with "bite blocks" have been developed. These devices often have a plate for holding the sensor and another plate that the patient bites down upon to position the device and the carried sensor. A bite block is shown for example, in U.S. Pat. No. 3,473,026.

Different sensors are often used depending upon the area of the mouth to be examined. This may include for example, endo, posterior, anterior, left, right, upper and lower bite wings, and the like. Known bite blocks and sensor holders have been individually designed and manufactured for each different type of sensor. The dimensions of the sensor and the holder dictate the degree of secured positioning of the sensor in the holder.

A dental professional may have a large number of x-ray sensors with varying sizes and shapes, and hence, a similarly large number of sensor holders. The dental professional is often faced with employing a different sensor or set of sensors, holders and bite blocks depending upon the particular x-ray procedure being employed. At best, it is time consuming to change between sensors, sensor holders and bite blocks.

A need exists therefore, for a sensor holder/bite block assembly or apparatus, which will accommodate different sizes and shapes of x-ray sensors. It has also been found that a need exits for an aiming ring that will accommodate more than one size or shape of dental x-ray collimator.

SUMMARY OF THE INVENTION

It is an object of the invention to provide a dental x-ray bite block.

It is another object of the invention to provide a bite block having an x-ray sensor holder.

It is a further object of the invention to provide a bite block and sensor holder assembly, which can be employed to hold a variety of sensors of different shapes or sizes.

It is yet another object of the invention to provide such a modular bite block which will detachably connect to a sensor holder.

These and other objects of the present invention, as well as the advantages thereof over existing art forms, which will become apparent in view of the following specification are accomplished by means hereinafter described and claimed.

In general, a dental bite block and sensor holder assembly comprises a bite block configured to detachably affix to a sensor holder. Affixing means are provided between the bite block and the sensor holder such that the sensor holder is removably affixed to the bite block.

Preferred forms of the subject dental bite block and sensor holder assembly are shown by way of example in the accompanying drawings, and are deemed sufficient to affect a full disclosure of the invention. The exemplary assembly is described in detail without attempting to show all of the various forms and modifications in which the invention might be embodied; the invention being measured by the appended claims and not by the details of the specification.

BRIEF DESCRIPTION OF THE DRAWINGS

FIG. 4 is an alternative embodiment of the sensor holder portion of the invention as depicted in FIG. 1;

PREFERRED EMBODIMENTS FOR CARRYING OUT THE INVENTION

Figure 1:
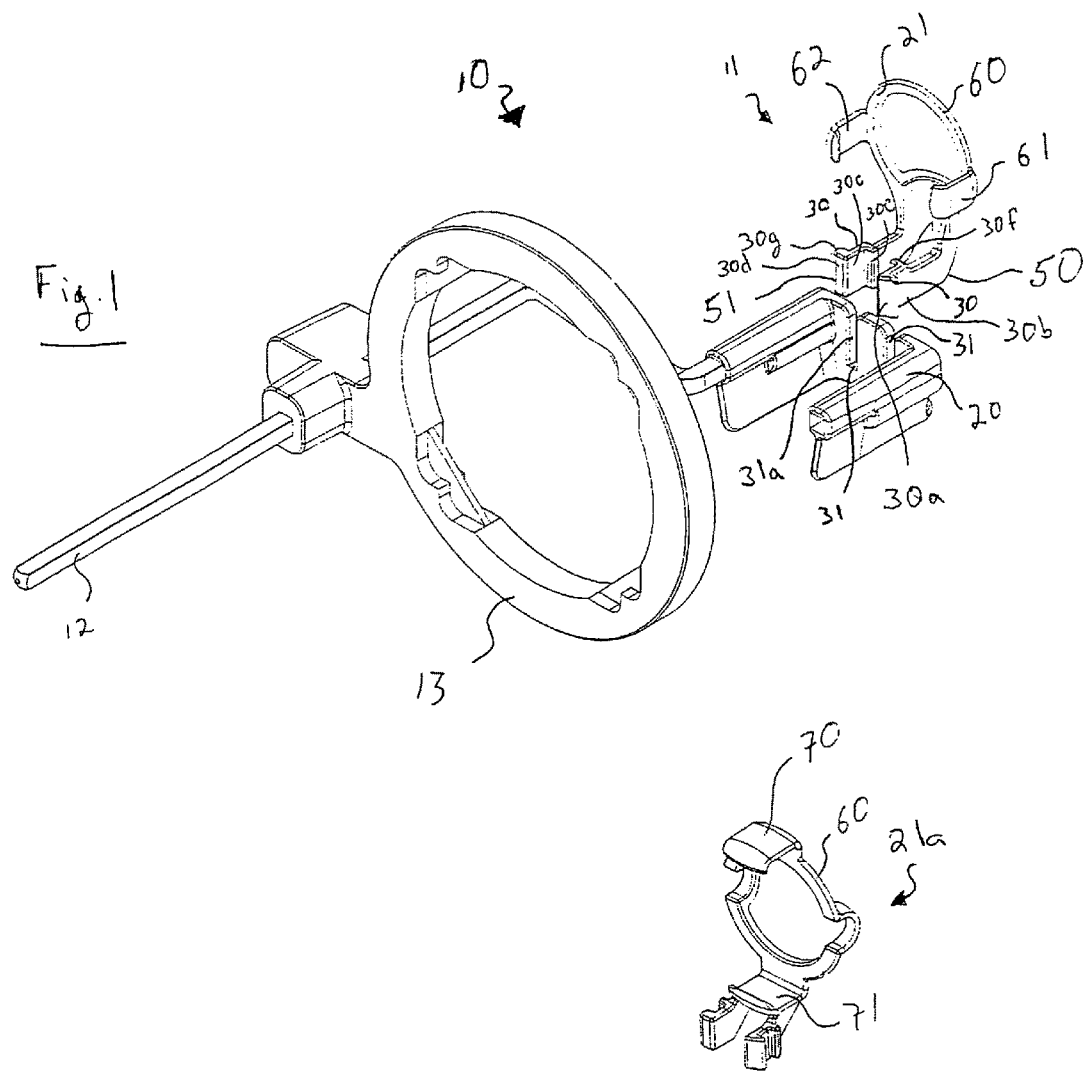
FIG. 1 is a perspective, exploded view of a bite block and sensor holder assembly, embodying the concepts of the present invention.
Figure 2:
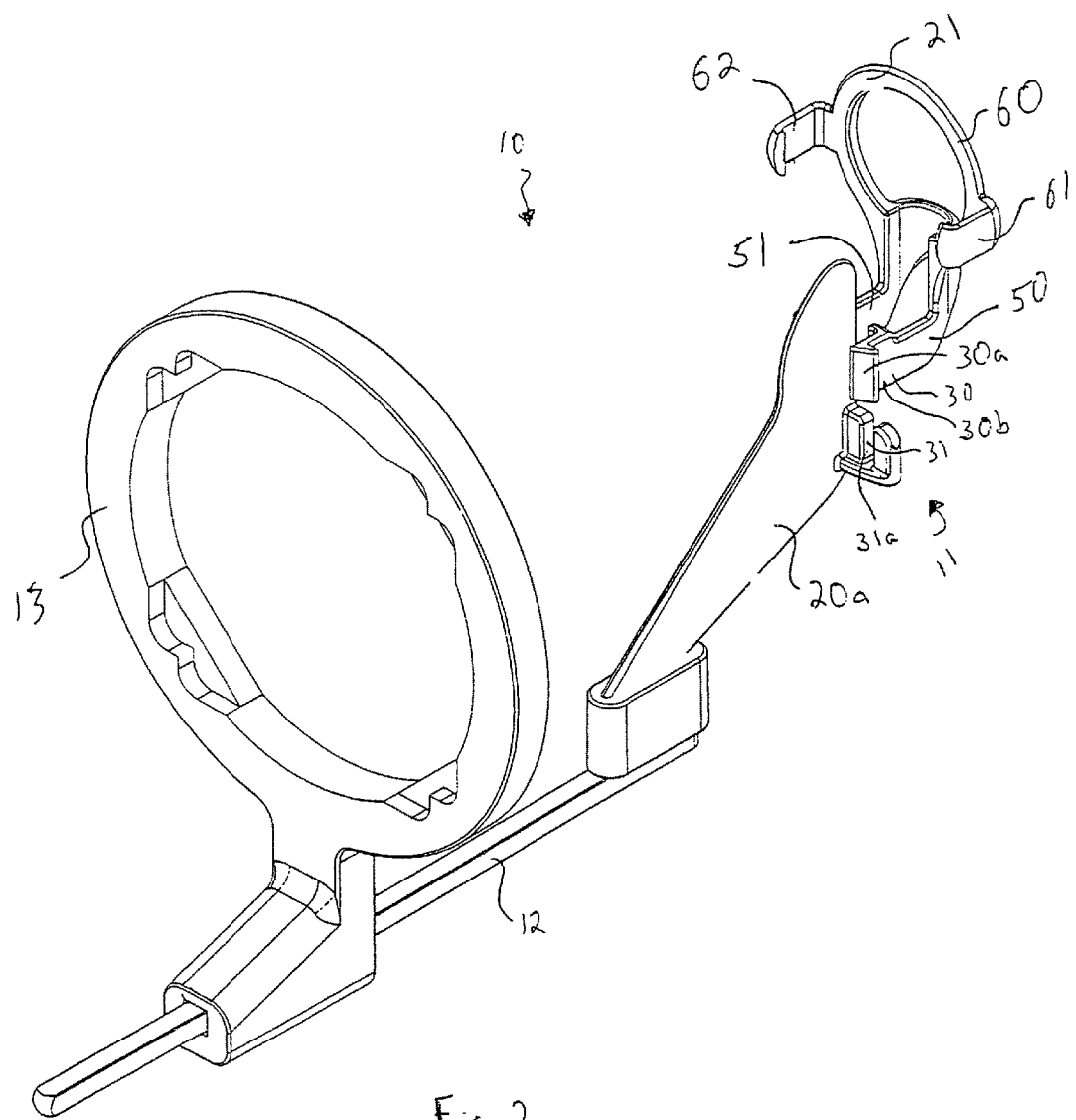
FIG. 2 is a perspective, exploded view of an alternative embodiment of a bite block and sensor holder assembly, also embodying the concepts of the present invention.
Figure 3:
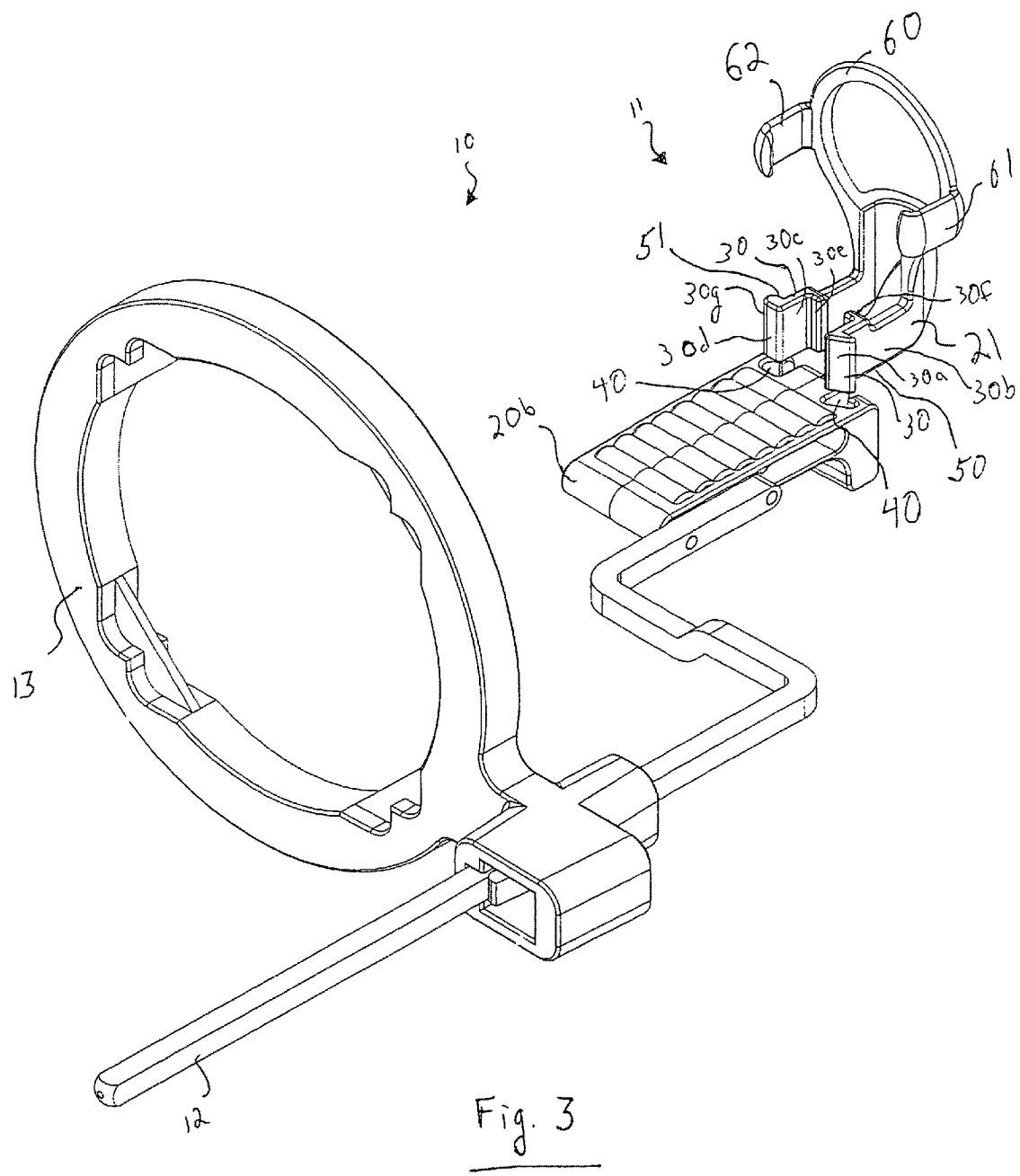
FIG. 3 is a perspective, exploded view of another alternative embodiment of a bite block and sensor holder assembly, also embodying the concepts of the present invention.

An x-ray sensor-positioning device according to the invention is generally designated by the number 10 on the attached drawings. Assembly 10 is preferably configured to have a conventional dental x-ray support or guide arm 12. An exemplary guide arm and its use with a bite block for taking a dental x-ray is shown in U.S. Pat. No. 3,473,026, which is incorporated by reference for its disclosure of a guide arm and bite block. As shown in FIGS. 1-3, guide arm 12 may be configured to be affixable to an x-ray tube collimator-positioning ring 13 in a conventional manner. Such a ring is also shown for example, in U.S. Pat. No. 3,473,026 and, U.S. Des. 237,016 which are incorporated by reference for disclosure of such a ring.

Figure 5:
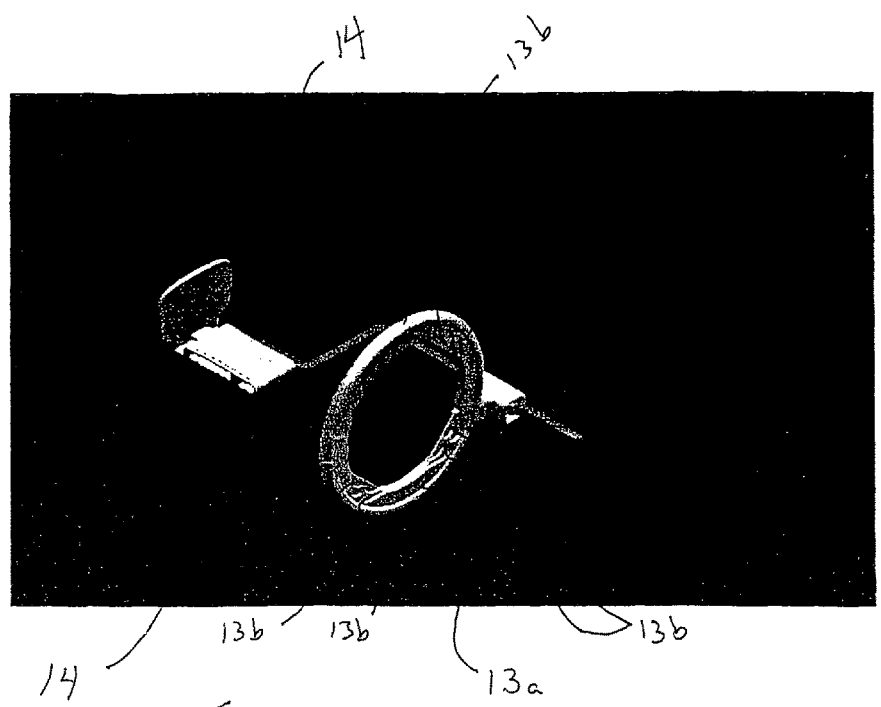
FIG. 5 is an alternative embodiment of an aiming ring and bite block assembly according to the invention.

Aiming ring 13a, FIG. 5, shows a plurality of regularly spaced, opposing steps 13b for receiving and registering a collimator (not shown). One set of such steps is known in the art (see for example, U.S. Des. 237,016). One embodiment of the present invention employs two sets of steps 13b in order to allow registration of more than one size of collimator. Although it is preferred to "concentrically" arrange one set of steps 13b within another, sets of steps 13b can be offset if desired. Grooves 14 can be provided in the exterior diameter of aiming ring 13a, such that an x-ray tubehead (not shown) can be aligned to wholly encompass whatever x-ray sensor is held by positioning device 10.

A bite block and sensor holder assembly 11 is provided as part of device 10, and includes a bite block 20 and a sensor holder 21 (FIG. 1). Bite block 20 is generally configured for use in a specific x-ray procedure. For example, bite block 20 in FIG. 1 is of a configuration useful for an endo x-ray. Bite block 20a (FIG. 2) is suited for use in taking a bitewing x-ray, and FIG. 3 shows a bite block 20b useful in taking an anterior or posterior x-ray image. Each bite block 20, 20a and 20b serve the same function, which is providing an area that is clamped between a patient's teeth. Given the requirements of a specific x-ray however, different shapes of bite blocks are required. The invention will be exemplified herein with reference to bite block 20 of FIG. 1 for purposes of this discussion (unless otherwise noted), it being understood that the invention is equally useful with bite blocks 20a, 20b or indeed, any conventional bite block shape or size without limitation.

There is removably attached to bite block 20 the sensor holder 21. It is likely that a dental professional will use one size and shape of sensor, be it x-ray film, CCD or phosphor plate technology for different x-rays (endo, anterior, posterior, bitewing or the like). Before the present invention, it would be standard practice for the dental professional to have a variety of bite block/sensor holders integrally formed together. According to the present invention, the sensor holder 21 and the bite block 20 are not integrally formed but rather detachably affixed. Further, the structure to attach a sensor holder 21 to a bite block 20 (which will be discussed and exemplified below), is the same no matter what the shape of the given bite block 20, 20a or 20b. In this manner, it will be appreciated that a single sensor holder can be used to attach to a different bite block 20, 20a or 20b. This is termed a "modular" design for purposes of this discussion. It will also be appreciated that a bite block may be used with different sizes and shapes of sensor holders. Again, the invention will be exemplified herein with respect to a single sensor holder 21.

To be detachably affixed to a bite block 20, sensor holder 21 must be provided with attachment means that correspond to attachment means carried by the bite block 20. By providing bite block 20 with the same attachment means as bite blocks having other shapes, such as bite blocks 20a and 20b, the same sensor 21 can be detachably affixed to any bite block 20, 20a or 20b, or indeed, any bite block carrying the same attachment means.

Any attachment means between sensor holder 21 and bite block 20 is within the scope of the invention, the only criteria being that the two components be held securely with respect to each other and that they be removable. Again, this aspect is termed being "modular" in design. A preferred attachment means is a complex profile or tab 30 carried by sensor holder 21 and an at least partially corresponding slot 31 carried by bite block 20. It is understood that bite block 20 could easily be configured to carry complex profile 30 and that sensor holder 21 could carry slot 31 and still be within the scope of the invention. The invention will be exemplified with sensor 21 carrying complex profile 30.

By "complex profile" it is meant a plurality of surfaces, such as surfaces 30a-30f (FIG. 1) each at some angle to at least one other. Complex profile tabs 30 and corresponding slots 31 can also be round and still fall within the scope of the definition of "complex profile". Surfaces 30a-f of complex profile 30 need not necessarily be linear, but may be curvilinear, such as surface 30g, or even round. By "slot" it is meant some surface such as surface 31a configured to receive at least one surface of complex profile 30 such as surface 30c.

Preferably, slot 31 is configured to receive complex profile 30 in such a manner that a plurality of surfaces 30a-f physically engage or touch slot 31 and at least some other portion of bite block 20. By properly configuring the actual dimensions of these components, sensor 21 can be held securely to bite block 20. The fit between complex profile 30 and slot 31 may also be a friction fit. It will be appreciated that to secure sensor 21 to bite block 20, complex profile 30 is received within slot 31. To detach or remove sensor 21 from bite block 20, it is merely necessary to slide complex profile 30 from slot 31.

An alternative embodiment of slot 31 is shown by way of example in FIG. 3 as slot 40. Slot 40 is itself also of a "complex profile" substantially corresponding in shape and dimension to the shape and dimension of complex profile 30.

It is also to be appreciated that complex profile 30 may be configured to have a plurality of arms 50 and 51, each carrying its own complex profile 30. In the embodiment of the invention depicted in the drawings, sensor 21 has two arms 50 and 51, it being understood that any number of arms is within the scope of the invention. It is also to be appreciated that any means of detachably affixing sensor 21 to bite block 20 is within the scope of the invention. This may include bolts, screws, nuts, locking mechanisms, or the like without limitation, all of which are within the scope of the invention and the term "modular."

Sensor holder 21 will be configured to receive one or more sensors. For example, in the sensor 21 depicted in FIGS. 1-3, a back support 60 and clip arms 61, 62 are employed. A sensor (not shown) can be secured within sensor 21. Because any sensor holder of any configuration is within the scope of the invention, and because such sensor holders are conventional in the art, no specific sensor holder, or bit block, is necessarily a limitation of the present invention.

For example, FIG. 4 depicts an alternative embodiment of a sensor holder 21a. Sensor holder 21a is configured with a back support 60 similar to back support 60 of sensor 21. However, in place of clip arms 61 and 62 of sensor 21, sensor 21a is provided with upper clip arm 70, generally opposing a lower clip arm 71. A conventional sensor (again, not show) is supported between clip arms 70, 71 and back support 60. Otherwise, sensor 21a is substantially similar in its modular design to sensor 21.

Figure 6:
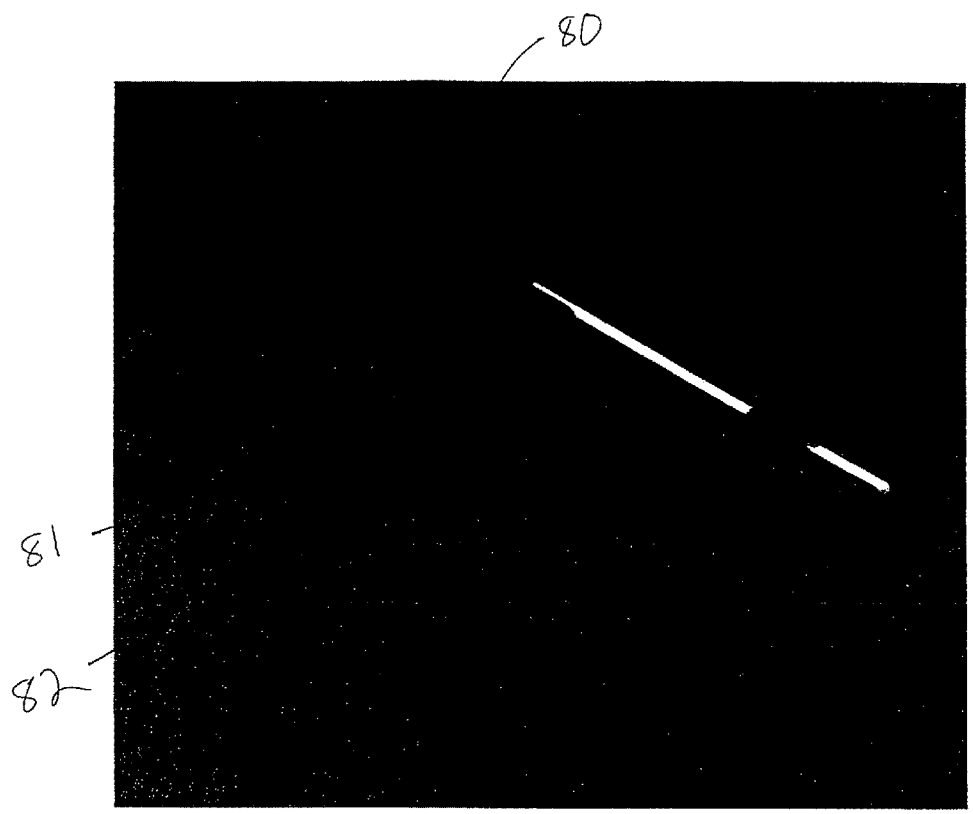
FIG. 6 is an alternative embodiment of an aiming ring and bite block assembly according to the invention.
Figure 7:
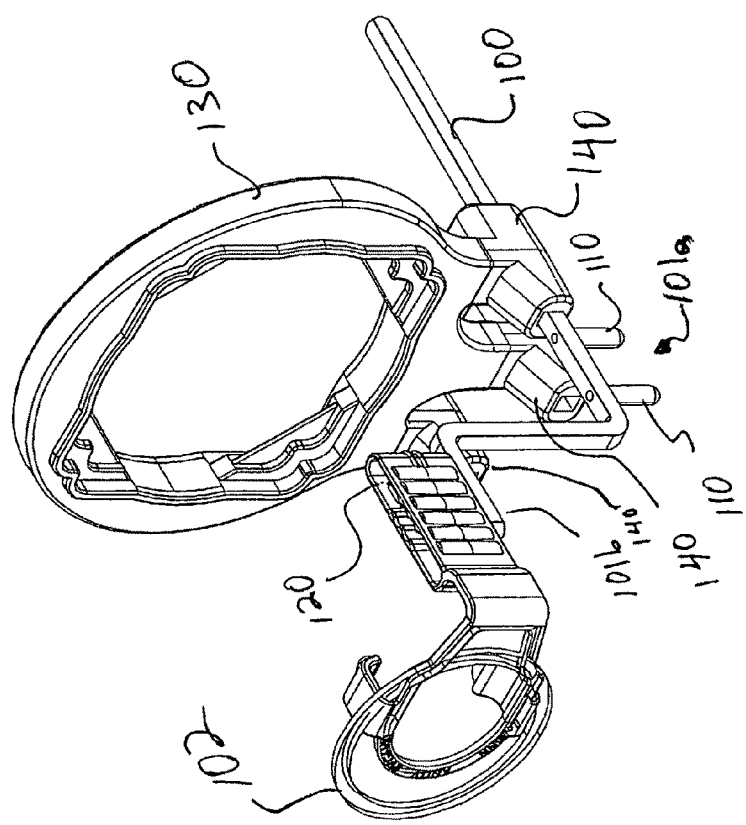
FIG. 7 is a perspective view of an alternative embodiment of a sensor folder assembly according to the present invention.
Figure 8:
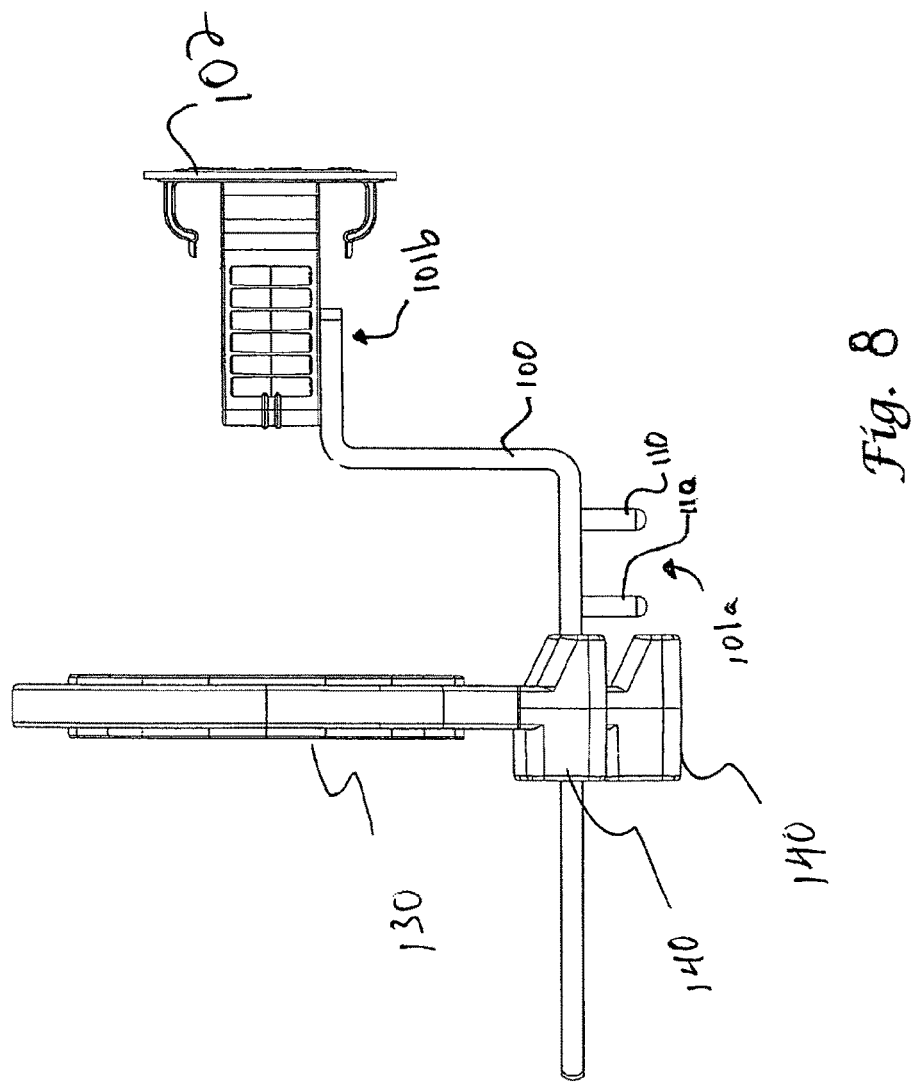
FIG. 8 is a top plan view of the assembly of FIG. 7.
Figure 9:
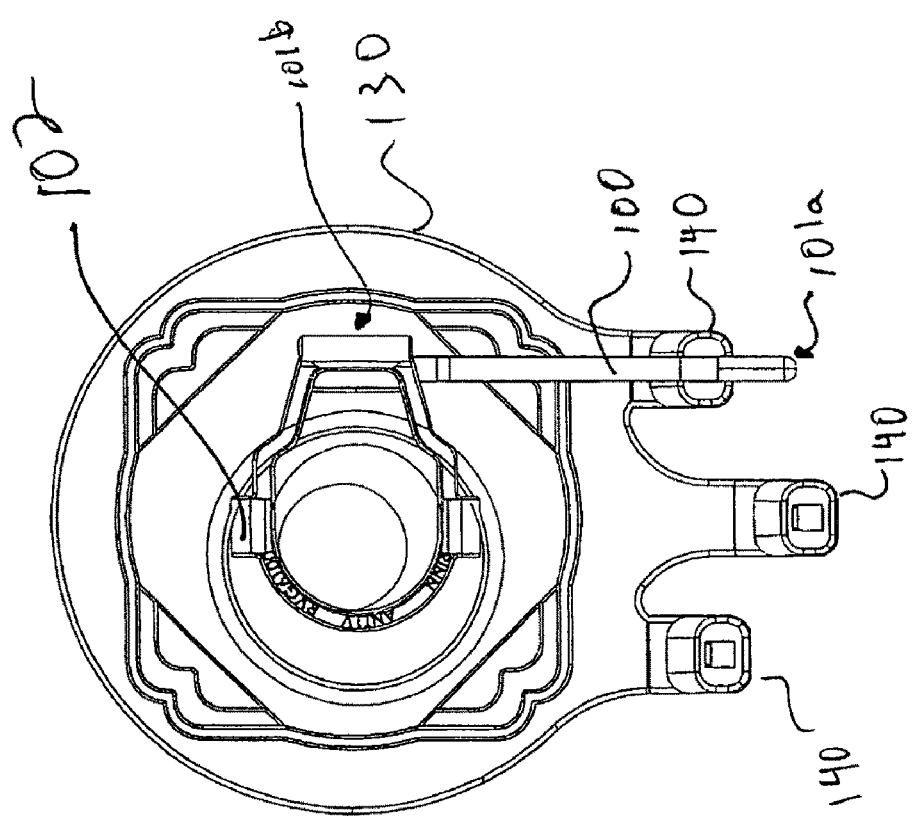
FIG. 9 is an end view of the assembly of FIG. 7.
Figure 10:
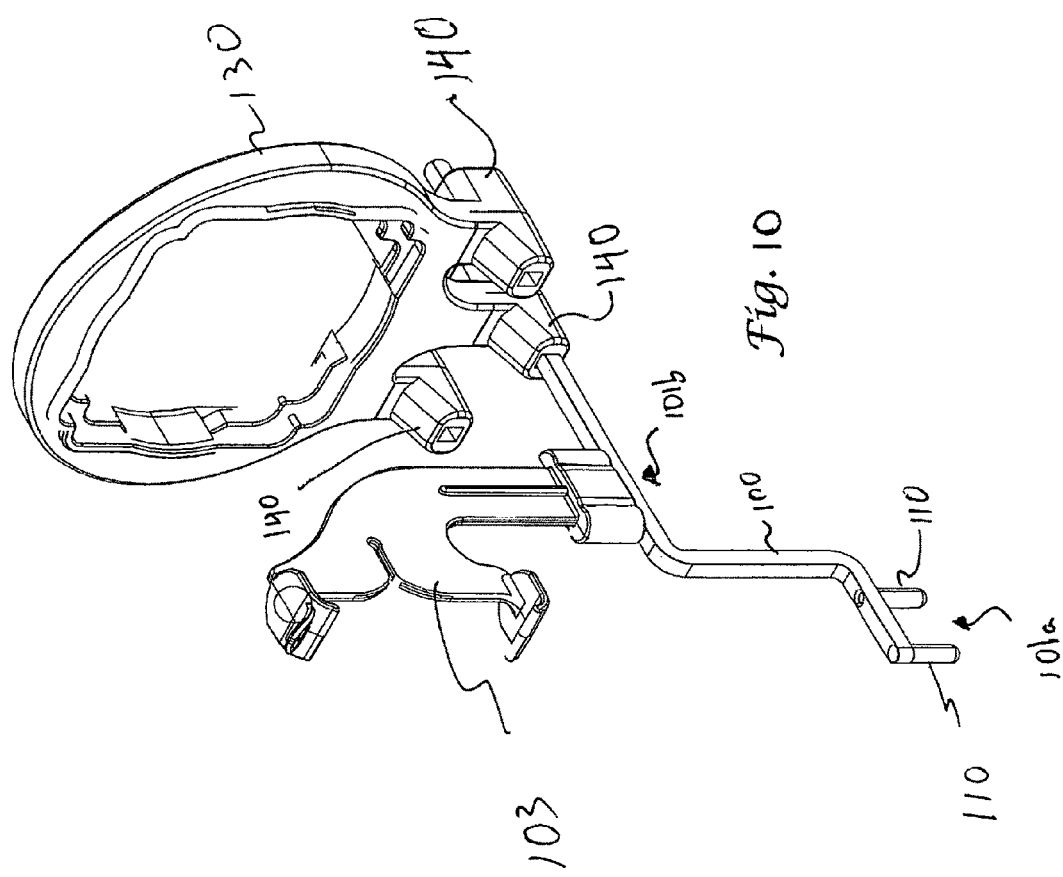
FIG. 10 is an alternative embodiment of an aiming ring and bite block assembly according to the invention.
Figure 11:
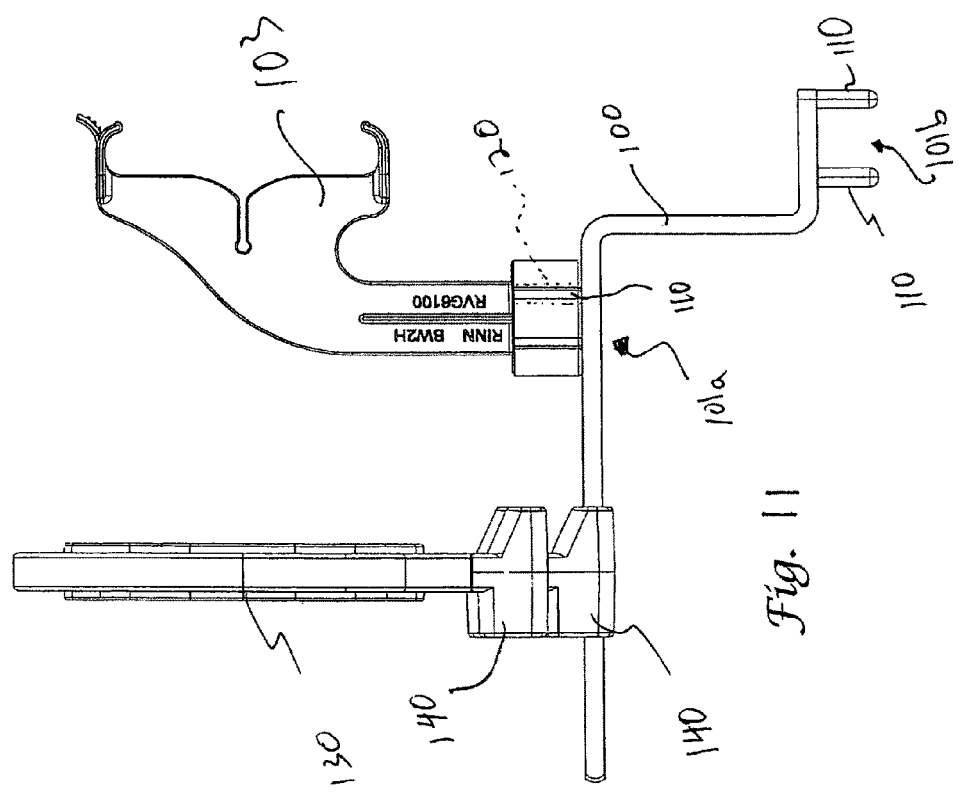
FIG. 11 is a top plan view of the assembly of FIG. 10.
Figure 12:
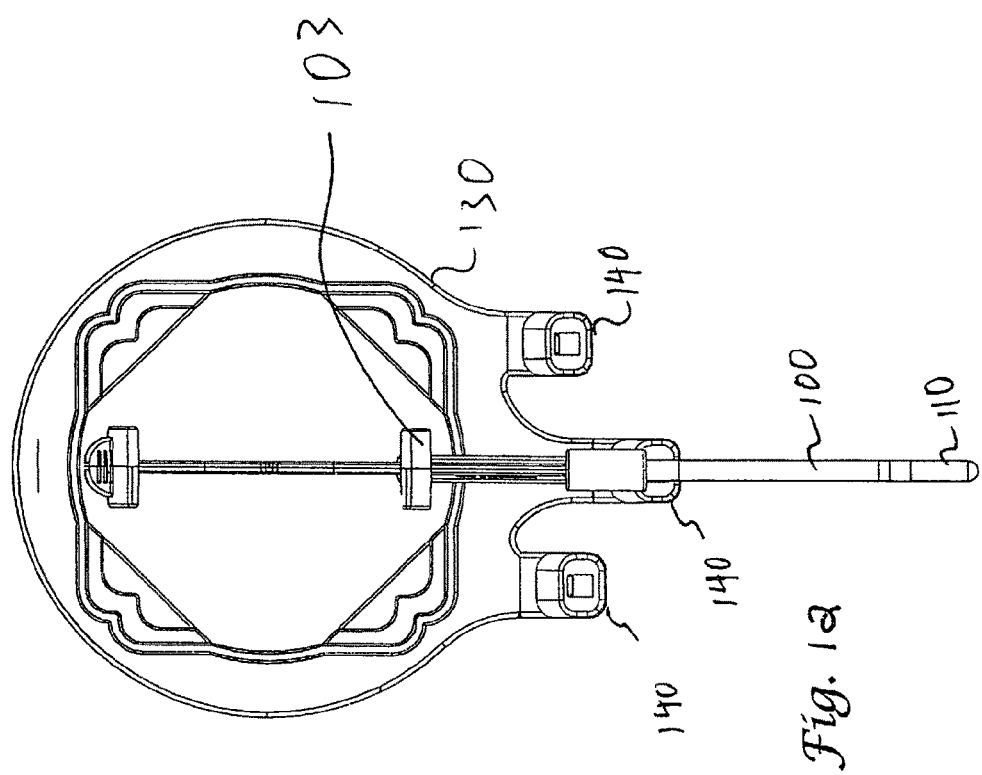
FIG. 12 is an end view of the assembly of FIG. 10.
Figure 13:
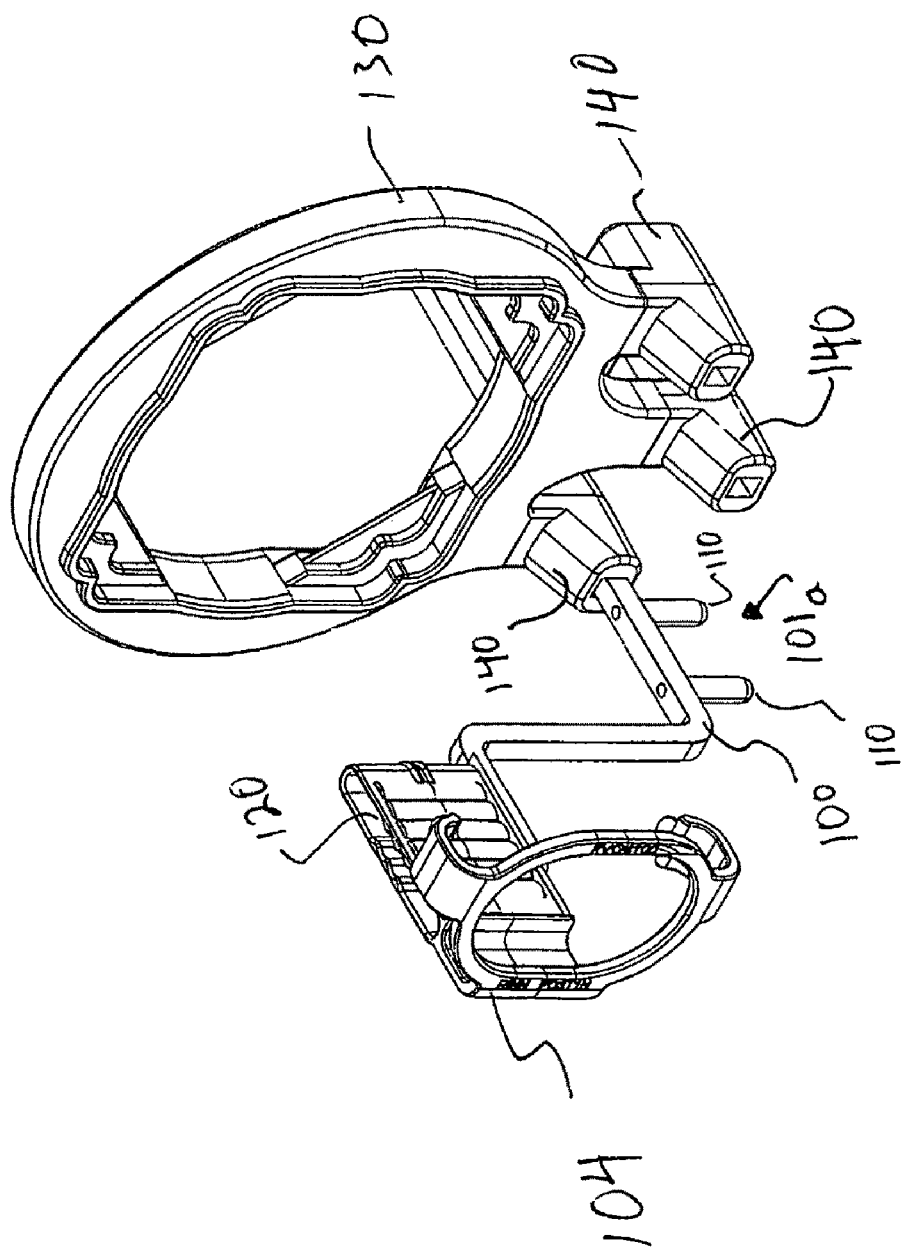
FIG. 13 is a perspective view of an assembly as in FIG. 7 showing the assembly in a different configuration than FIG. 7.
Figure 14:
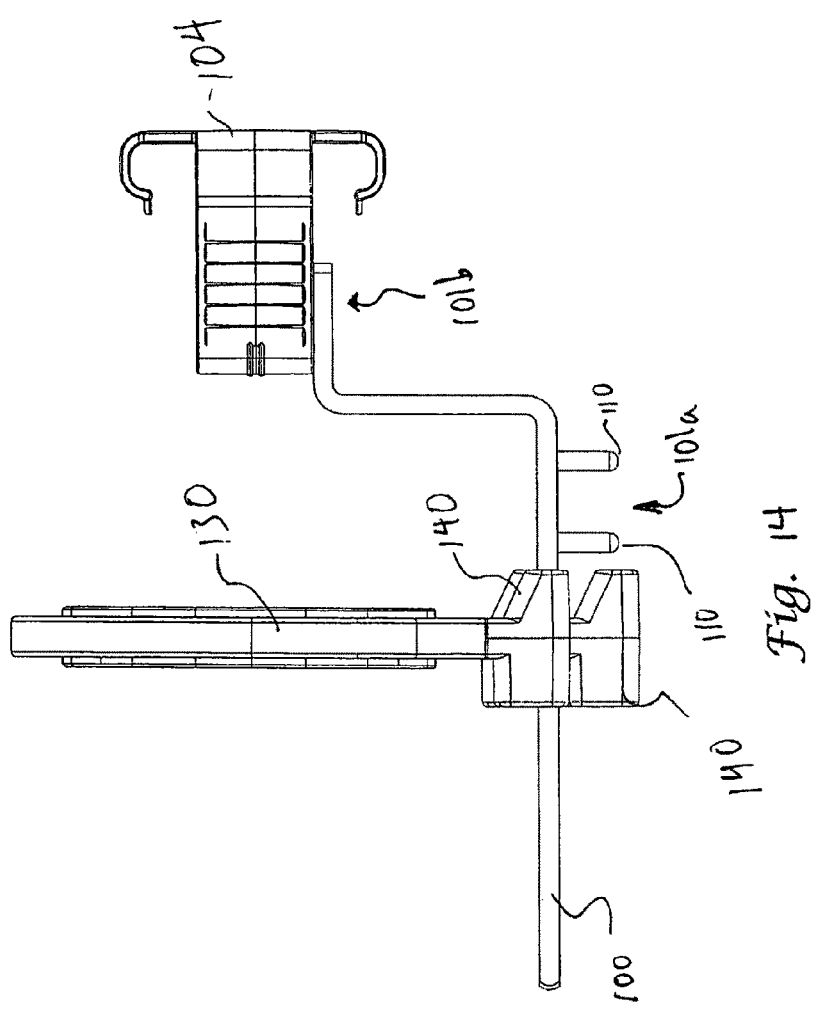
FIG. 14 is a top plan view of the assembly of FIG. 13.
Figure 15:
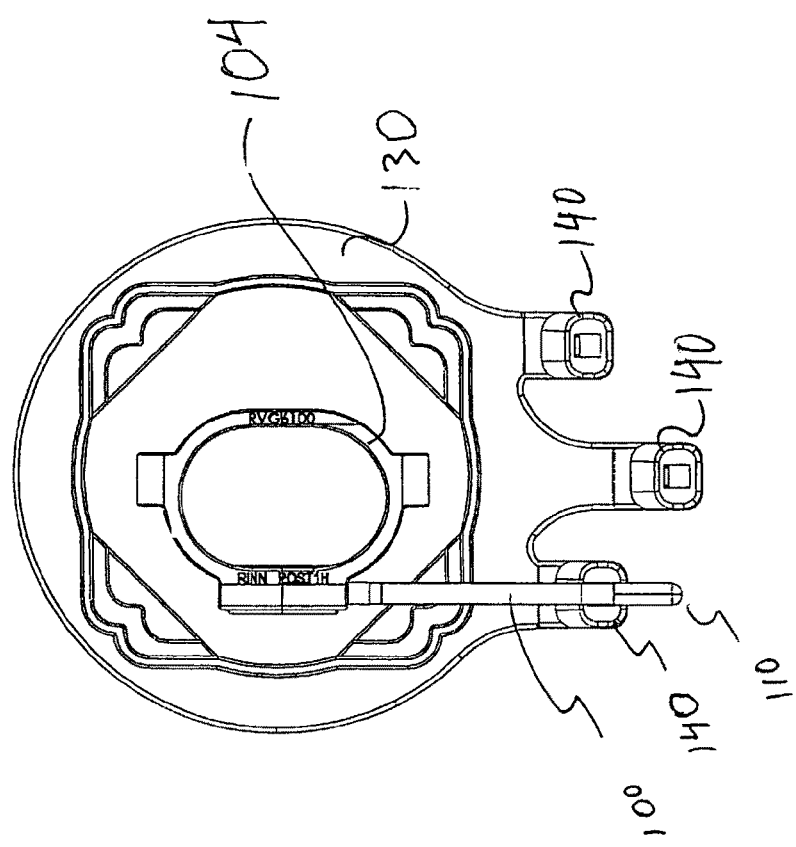
FIG. 15 is an end view of the assembly of FIG. 14.
Figure 16:
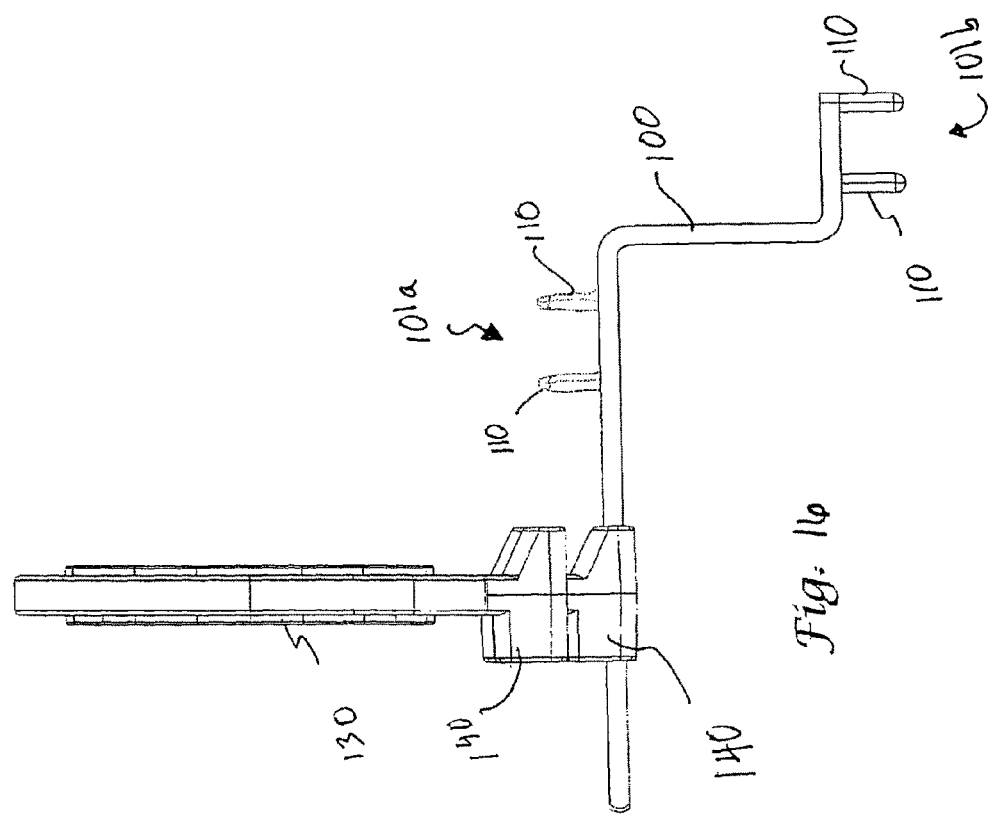
FIG. 16 is view of a support or guide arm according to an embodiment of the present invention and showing an aiming ring affixed thereto.

FIG. 6 shows an alternative embodiment of a bitewing block 80. Bitewing 80 is provided with a groove 81 on the bite surface 82 to help the user in positioning a sensor (not shown) held by block 80. Groove 81 helps to register which such a sensor. It will also be appreciated that block 80 is of an overall thin design, allowing for greater patient comfort as compared to prior bite blocks.

According to another embodiment of the present invention, a guide arm 100 may be provided with a plurality of attachment sites 101a and 101b for a given sensor holder 102, 103 and 104 (FIGS. 7-16). In the embodiment shown in the drawings, an attachment site 101a or 101b may include one or more pins 110 which can be physically received within a corresponding aperture 120 in a given sensor holder 102-104. In the preferred embodiment, the pins are retained within a given aperture 120 by a friction fit, which may be overcome by a user to remove the sensor holder 102-104 therefrom if desired. As will be appreciated, the size and shape of pins 110 and apertures 120 may vary, and other means of affixing a sensor holder 102-104 to a site 101a, 101b or a guide arm 100 may be employed and still be within the scope of the invention. By providing a plurality of attachment sites 101a, 101b a plurality of dental x-ray images may be taken with the same components. For example, anterior, posterior and bitewing images may be taken. It is an advantage to the user that all such images may be taken with the use of one guide arm 100. By using one guide arm 100, less cleaning and expense is required on behalf of the dental professional. The chances of spreading communicable diseases and germs between patients is reduced because a smaller number of components are needed for a given x-ray procedure. It will be further appreciated that various components for different assemblies can be provided in a kit form, allowing the professional to take different x-ray images employing a single guide arm and other components.

According to an embodiment of the invention, various components can be color-coded or provided with other indicia (not shown) to indicate which sensor holder is used for a given x-ray procedure. Pins 110 of a given site 101a or 101b may be so coded to indicate which sensor holder 102-104 is used for the desired procedure.

In still another embodiment of the invention, a guide ring 130 is provided with a plurality of journals 140 for receiving guide arm 100 therein in preferably, a friction fit manner. Journals 140 may also be coded such as by color or other indicia (not shown) in order to indicate which journal is used for a given x-ray procedure, as with the other such coded components discussed hereinabove.

Based upon the foregoing disclosure, it should now be apparent that the use of the modular bite block, sensor holder assembly and guide arm described herein will carry out the objects set forth hereinabove. It is, therefore, to be understood that any variations evident fall within the scope of the claimed invention and thus, the selection of specific component elements or parts can be determined without departing from the spirit of the invention herein disclosed and described. Thus, the scope of the invention shall include all modifications and variations that may fall within the scope of the attached claims.

What is claimed is:

1. A kit for use in dental imaging procedures to align an image receptor holder with a collimator while taking an image of a patient's dentition, the kit comprising: a support arm and a plurality of image receptor holders wherein at least two of said image receptor holders are used for taking images of different parts of the patient's dentition; said support arm comprising at least a first attachment pin and a second attachment pin; each of said plurality of image receptors having a pin-receiving aperture for receiving at least one of said attachment pins such that one of said at least two of said image receptor holders is removably affixed to said support arm by receiving said first attachment pin within said aperture therein, and the other of said at least two of said image receptor holders is removably affixed to said support arm by receiving said second attachment pin within said aperture therein.

2. A kit as in claim 1, wherein plurality of image receptor holders include at least one said holder for taking of an anterior, posterior and bite-wing image of the patient's dental arch.

3. A kit as in claim 1 wherein said support arm comprises a first attachment pin mate pin.

4. A kit as in claim 1 wherein said support arm comprises a second attachment pin mater pin.

5. A kit as in claim 1 wherein said support arm comprises a bar with a plurality of bends such that said bar has at least one planar dimension.

6. A kit as in claim 5, wherein at least one of said attachment pins is also within said planar dimension.

7. A kit as in claim 6 wherein said support arm comprises at least a first and a second bend, such that said bar has a first length contiguously formed with a first bend elbow, said first bend elbow contiguously formed with an second length, said second length contiguously formed with a second bend elbow, and said second bend elbow being contiguously formed with a third length.

8. A kit as in claim 7 wherein said first attachment pin is affixed to said first length and said second attachment pin is affixed to said third length.

9. A kit as in claim 1, wherein said first or second pin is indicia-coded with a complementary one of said image receptor holders.

10. A kit as in claim 1, further comprising a collimator ring.

11. A kit as in claim 10 wherein said collimator ring has a collimator positioning ring and a support arm receiving socket.

12. A kit as in claim 11 wherein said collimator ring is round, oval, square, rectangular, trapezoidal or triangular in shape.

13. A kit as in claim 12 wherein said collimator ring comprises a plurality of said support arm receiving sockets such that the collimator may be aligned in one of a like plurality number of positions.

14. A method of taking dental images of a patient's dentition comprising the step of:
providing a support arm having a plurality of image receptor holder attachment points, each said attachment point enabling the taking of a preselected dental image;
removably affixing an image receptor holder to said support arm at one of said attachment points;
wherein each said attachment point comprises at least one attachment pin configured to be received within a complementary-shaped aperture in at least one of said image receptor holders;
wherein said support arm comprises at least two of said attachment pins at least one of said attachment points, and said image receptor holder comprises at least to complementary said apertures; and
wherein said support arm comprises at least two of said sets of pins, such that at least one of said image receptor holders can be removably affixed to one of said at least two sets of pins and at least one other of said image receptor holders can be removably affixed to the other of said at least two sets of pins.

* * * * *